US009750694B2

(12) United States Patent
Takeuchi et al.

(10) Patent No.: US 9,750,694 B2
(45) Date of Patent: Sep. 5, 2017

(54) TRANSPULMONARY LIPOSOME FOR CONTROLLING DRUG ARRIVAL

(71) Applicants: Hirofumi Takeuchi, Gifu-shi, Gifu (JP); OTSUKA PHARMACEUTICAL CO., LTD., Tokyo (JP)

(72) Inventors: Hirofumi Takeuchi, Gifu (JP); Koji Nakano, Gifu (JP); Hidekazu Toyobuku, Tokushima (JP)

(73) Assignees: Hirofumi Takeuchi, Gifu-Shi, Gifu (JP); OTSUKA PHARMACEUTICAL CO., LTD., Chiyoda-ku, Tokyo (JP)

( * ) Notice: Subject to any disclaimer, the term of this patent is extended or adjusted under 35 U.S.C. 154(b) by 0 days.

(21) Appl. No.: 14/108,826

(22) Filed: Dec. 17, 2013

(65) Prior Publication Data

US 2014/0105968 A1  Apr. 17, 2014

Related U.S. Application Data

(63) Continuation of application No. 12/593,827, filed as application No. PCT/JP2008/056156 on Mar. 28, 2008, now Pat. No. 8,658,204.

(30) Foreign Application Priority Data

Mar. 30, 2007  (JP) ................................. 2007-090874

(51) Int. Cl.
*A61K 47/32* (2006.01)
*A61K 47/36* (2006.01)
*A61K 9/127* (2006.01)
*A61K 9/00* (2006.01)
*A61K 45/06* (2006.01)
*C12N 15/88* (2006.01)
*A61K 48/00* (2006.01)

(52) U.S. Cl.
CPC ............ *A61K 9/1277* (2013.01); *A61K 9/007* (2013.01); *A61K 9/0078* (2013.01); *A61K 9/1271* (2013.01); *A61K 45/06* (2013.01); *A61K 47/32* (2013.01); *A61K 47/36* (2013.01); *A61K 48/0075* (2013.01); *C12N 15/88* (2013.01); *A61K 48/00* (2013.01); *C12N 2810/10* (2013.01)

(58) Field of Classification Search
CPC ........ A61K 45/06; A61K 47/32; A61K 47/36; A61K 48/00; A61K 48/0075; A61K 9/007; A61K 9/0078; A61K 9/1271; A61K 9/1277; C12N 15/88; C12N 2810/10
USPC ........................................................ 424/450
See application file for complete search history.

(56) References Cited

U.S. PATENT DOCUMENTS

| 2002/0012998 A1 | 1/2002 | Gonda et al. |
| 2003/0096774 A1 | 5/2003 | Gonda et al. |
| 2006/0002992 A1 | 1/2006 | Schmehl et al. |

FOREIGN PATENT DOCUMENTS

| CN | 1582932 | 2/2005 |
| JP | 4503953 | 7/1992 |
| JP | 2003528131 | 9/2003 |
| JP | 2005-298407 A | 10/2005 |
| RU | 2130771 C1 | 5/1999 |
| RU | 2238091 C2 | 10/2004 |
| WO | 9007469 | 7/1990 |
| WO | 01/03668 A1 | 1/2001 |
| WO | 01/72283 A1 | 10/2001 |
| WO | 2004/110493 A2 | 12/2004 |

OTHER PUBLICATIONS

Takeuchi et al. (Advanced Drug Delivery Review, 47, 2001, pp. 39-54).*
Takeuchi et al. (Journal of Control Release 68, 2000, 195-205).*
Sato et al. Biomaterials, vol. 22, 2001, 2075-2080.*
H. Yamamoto, "Peptide no Keinenmaku Toyo o Mezashita Seibunkaisei Biryushieseizai no Sekkei", Annual Proceedings of Gifu Pharmaceutical University, vol. 49, pp. 23-32, 2000.
Y. Kawashima, "Nan'yokaisei Yakubutsu ya Peptide-sei Yakubutsu o Taisho ni shita Keinenmaku (Keihai ya Keiko) Toyoyo Shinki Nano Ryushi Carrier System ni yoru DDS (Yakubutsu Sotatsu System) no Saiteki Sekkeiho no Kaihatsu to Taikeika", Research Reports of Uehara Memorial Foundation, vol. 17, pp. 1-3, 2003.
H. Takeuchi, et al., "Yakubutsu Carrier to shite no Liposome, Piddo Maikuro Sufea ni Kansuru Seizaigakuteki Kenkyu", Hyomen, vol. 32, No. 6, pp. 423-429, Jun. 1, 1994.
T. Sato, et al., "In vitro gene delivery mediated by chitosan. Effect of pH, serum, and molecular mass of chitosan on the transfection efficiency", Biomaterials, vol. 22, pp. 2075-2080, 2001.
H. Takeuchi, et al., "Physical stability of size controlled small unilameller liposomes coated with a modified polyvinyl alcohol", International Journal of Pharmaceuticals, vol. 164, pp. 103-111, 1998.

(Continued)

*Primary Examiner* — Janet Epps-Smith
(74) *Attorney, Agent, or Firm* — Sughrue Mion, PLLC

(57) ABSTRACT

An object of the present invention is to provide a liposome which is excellent in intrapulmonary delivery controllability of drugs or genes and is suited for pulmonary administration. By modifying the surface of a liposome using a terminal hydrophobized polyvinyl alcohol and/or chitosan, retention of drugs or genes encapsulated in the liposome on the surface of lung tissue and transfer of drugs or genes into lung tissue can be properly modulated, and thus in vivo behavior can be controlled.

5 Claims, 1 Drawing Sheet

(56) References Cited

OTHER PUBLICATIONS

H. Takeuchi, et al., "Polymer coating of liposomes with a modified polyvinyl alcohol and their systemic circulation and RES uptake in rats", Journal of Controlled Release, vol. 68, No. 2, pp. 195-205, 2000.
H. Takeuchi, et al., "Mucoadhesive nanoparticulate systems for peptide drug delivery", Advanced Drug Delivery Reviews, vol. 47, No. 1, pp. 39-54, Mar. 23, 2001.
H. Takeuchi, et al., "Effectiveness of submicron-sized, chitosan-coated liposomes in oral administration of peptide drugs", International Journal of Pharmaceuticals, vol. 303, pp. 160-170, Oct. 13, 2005.
H. Takeuchi, et al., "Evaluation of circulation profiles of liposomes coated with hydrophilic polymers having different molecular weights in rats", Journal of Controlled Release, vol. 75, pp. 83-91, Jul. 10, 2001.
Office Action issued in corresponding Russian Application No. 2009140058 dated Dec. 27, 2011.
Office Action issued in corresponding Russian Application No. 2009140058 dated May 15, 2012 (in the name of Otsuka Pharmaceutical Co., Ltd.).
D.G. Grahame-Smith et al., Oxford textbook of clinical pharmacology, Russian Edition, "Medicine", 2000, p. 331.
G.A Melentieva., Pharmaceutical Chemistry, M., Medicine, 1968, p. 166.
Extended Search Report dated Dec. 14, 2013, in corresponding European Patent Application No. 08739274.2.
Hirofumi Takeuchi et al., "Enteral Absorption of Insulin in Rats from Mucoadhesive Chitosan-Coated Liposomes", Pharmaceutical Research, 1996, 13(6): 896-901.
H. Takeuchi et al., "Mucoadhesive Liposomes Coated with Chitosan or Carbopol for Oral Administration of Peptide Drugs", Proceedings of the International Symposium on Controlled Release Bioactive Materials, 1999, 26: 988-989.
Hriofumi Takeuchi et al., "Prolonged circulation time of doxorubicin-loaded liposomes coated with a modified polyvinyl alcohol after intravenous injuection in rats", European Journal of Pharmaceutics and Biopharmaceutics, 1999, 48: 123-129.
Daan J.A. Crommelin et al., "Liposomes—Successful Carrier Systems for Targeted Delivery of Drugs", Business Briefing Pharmatech, 2003, pp. 209-213.
Hirofumi Takeuchi et al., "Novel mucoadhesion tests for polymers and polymer-coated particles to design optimal mucoadhesive drug delivery systems", Advanced Drug Delivery Reviews, 2005, 57: 1583-1594.
H. Oya Alpar et al., "Biodegradable mucoadhesive particulates for nasal and pulmonary antigen and DNA delivery", Advanced Drug Delivery Reviews, 2005, 57: 411-430.
Cryan, Sally-Ann,Carrier-based Strategies for Targeting Protein and Peptide Drugs to the Lungs; AAPS Journal 2005; pp. E20-E41; 7 (1) Article 4 (http://www.aapsj.org).
Australian Examination Report dated Aug. 9, 2013 issued in Australian Patent Application 2008233656.
Office Action for Mexican Application No. MX/a/2009/010479 dated Jan. 30, 2014 (with English Translation).

* cited by examiner

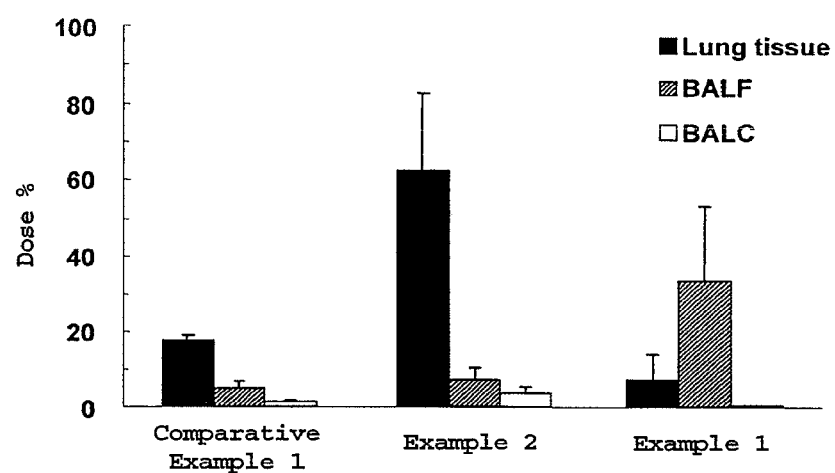

TRANSPULMONARY LIPOSOME FOR CONTROLLING DRUG ARRIVAL

CROSS REFERENCE TO RELATED APPLICATIONS

This is a Continuation Application of U.S. application Ser. No. 12/593,827 filed Sep. 29, 2009, which is a National Phase Application of PCT International Application No. PCT/JP2008/056156 filed Mar. 28, 2008, which claims priority based on Japanese Application No. 2007-090874 filed Mar. 30, 2007. The disclosures of the prior applications are incorporated herein by reference in their entirety.

TECHNICAL FIELD

The present invention relates to a liposome which is excellent in delivery controllability of drugs or genes and which is suitable for pulmonary administration. Furthermore, the present invention relates to a liposome preparation in which drugs or genes are encapsulated in the liposome.

BACKGROUND ART

A liposome is a closed vesicle having a lipid bilayer structure. A liposome can encapsulate drugs or genes in a state isolated from the external environment with a bimolecular membrane, and thus can protect the encapsulated drugs or genes from being decomposed or metabolized. In addition, a liposome can be attached to a cell membrane and mucous membrane by controlling the composition of the liposomal membrane, and thus it is possible to deliver the encapsulated drugs or genes into cells. Liposomes are attracting attention as a carrier for drugs or genes because of such protective function and delivery function.

In general, drugs and genes used for treatment of diseases are desired to be delivered to a target site of action and to exert an intended pharmacological action at such a site. Application of liposomes is attempted to improve delivery characteristics for drugs or genes to the target site of action. Means to control the kinds, ratio and surface charges of constituent lipids have been proposed to give liposomes a selective transport function to the target site of action. However, the above prior art methods cannot adequately control delivery characteristics for drugs under present circumstances. Particularly, drugs and genes applied to lung tissue are required to highly control in vivo behavior of drugs or genes depending on its mode of action, i.e., retention on the surface of lung tissue (e.g., on the bronchovesicular surface) is desired in some cases and incorporation inside lung tissue is desired in other cases. However, techniques to control in vivo behavior of drugs and genes in lung tissue are not established yet.

Meanwhile, techniques to modify the surface of liposomes with macromolecules such as polymers have been reported (e.g., Non-Patent Documents 1 and 2). However, techniques to control in vivo behavior of drugs or genes in lung tissue by modifying the surface of liposomes are not sufficiently known.

NON-PATENT DOCUMENT 1

Takeuchi H et al., "Effectiveness of submicron-sized, chitosan-coated liposomes in oral administration of peptide drugs", Int J. Pharm., 2005 Oct. 13; 303(1-2): 160-170

NON-PATENT DOCUMENT 2

Takeuchi H et al., "Evaluation of circulation profiles of liposomes coated with hydrophilic polymers having different molecular weights in rats", J Control Release., 2001 Jul. 10; 75(1-2): 83-91

DISCLOSURE OF THE INVENTION

Technical Problem

Thus, an object of the invention is to solve the above problems of the prior art. Specifically, an object of the invention is to provide a liposome which is excellent in delivery controllability of drugs or genes and which is suitable for pulmonary administration, and a liposome preparation for pulmonary administration in which drugs or genes are encapsulated in the liposome. Further, an another object of the invention is to provide a method for treating a disease of Lung tissue by using said liposome preparation.

Means for Solving the Problem

The present inventors have intensively studied so as to achieve the above object and found that, by modifying the surface of a liposome using a terminal hydrophobized polyvinyl alcohol and/or chitosan, retention of drugs or genes encapsulated in the liposome on the surface of lung tissue, and transfer of drugs or genes into lung tissue or lung surface cells can be properly modulated, and thus in vivo behavior of drugs or genes can be controlled. The invention has been completed by making further improvement based on these findings.

Namely, the present invention provides the following embodiments.

Item 1. A liposome for pulmonary administration, wherein the surface of the liposome is modified with at least one polymer selected from the group consisting of terminal hydrophobized polyvinyl alcohols and chitosan.

Item 2. The liposome for pulmonary administration according to Item 1, which contains a phospholipid as a constituent component of a liposomal membrane.

Item 3. The liposome for pulmonary administration according to Item 1, which contains phosphatidylcholine, cholesterol and a dialkyl phosphate ester as constituent components of a liposomal membrane.

Item 4. The liposome for pulmonary administration according to Item 1, wherein the surface of the liposome is modified with a terminal hydrophobized polyvinyl alcohol, and the lung tissue surface or surface cells are target sites of the liposome.

Item 5. The liposome for pulmonary administration according to Item 1, wherein the surface of the liposome is modified with a terminal hydrophobized polyvinyl alcohol, and the liposome is sustained release liposome for pulmonary administration.

Item 6. The liposome for pulmonary administration according to Item 1, wherein the surface of the liposome is modified with chitosan, and the surface and inside of lung tissue are target sites of the liposome.

Item 7. The liposome for pulmonary administration according to Item 1, wherein the surface of the liposome is modified with chitosan, and the liposome is fast-acting liposome for pulmonary administration.

Item 8. The liposome for pulmonary administration according to Item 1, wherein the surface of the liposome is modified with a terminal hydrophobized polyvinyl alcohol in which a hydrophobic group is an alkyl group having 1 to 30 carbon atoms, an alkoxy group having 1 to 30 carbon atoms, a carboxyalkyl group having 1 to 30 carbon atoms or an thioalkyl group having 1 to 30 carbon atoms.
}

Item 9. A liposome preparation for pulmonary administration, wherein a drug or a gene is encapsulated in the liposome for pulmonary administration of Item 1.

Item 10. The liposome preparation for pulmonary administration according to Item 9, wherein the surface of the liposome is modified with a terminal hydrophobized polyvinyl alcohol, and the lung tissue surface or surface cells are target sites of the liposome preparation.

Item 11. The liposome preparation for pulmonary administration according to Item 9, wherein the liposome is surface-modified with chitosan, and the surface and inside of lung tissue are target sites of the liposome preparation.

Item 12. A method for preparing a liposome preparation for pulmonary administration comprising the following steps (i) and (ii):

(i) mixing a drug or a gene with a constituent component or components of a liposomal membrane to obtain a drug or gene-encapsulating liposome, and (ii) mixing the drug or gene-encapsulating liposome obtained by above step (i) with at least one polymer selected from the group consisting of terminal hydrophobized polyvinyl alcohols and chitosan to modify the surface of the liposome with the polymer.

Item 13. Use of at least one polymer selected from the group consisting of terminal hydrophobized polyvinyl alcohols and chitosan for the manufacture of a liposome for pulmonary administration.

Item 14. Use of a terminal hydrophobized polyvinyl alcohol for the manufacture of a sustained release liposome for pulmonary administration.

Item 15. Use of chitosan for the manufacture of a fast-acting liposome for pulmonary administration.

Item 16. A method for treating a disease of lung tissue, comprising the step of administering to a lung of a patient suffering from the disease of lung tissue a therapeutically effective amount of the liposome preparation of Item 9.

Effects of the Invention

The liposome for transpulmonary administration of the invention can impart desired in vivo behavior to drugs or genes to be applied to lung tissue since retention of drugs or genes encapsulated in the liposome on the surface of lung tissue and transfer of drugs or genes into lung tissue can be controlled by modulating the amount of a terminal hydrophobized polyvinyl alcohol and/or chitosan. Therefore, according to the liposome for pulmonary administration of the invention, a pharmacologic action due to encapsulated drugs or genes can be effectively exerted at the target site of action of lung tissue.

It is considered that the liposome for pulmonary administration of the invention has comparatively high safety since the terminal hydrophobized polyvinyl alcohol and chitosan used for surface modification of the liposome for pulmonary administration of the present invention have biocompatibility or biodegradation characteristics. Further, according to the liposome for pulmonary administration of the invention, it is possible to protect the liposome by the terminal hydrophobized polyvinyl alcohol and/or chitosan with which the liposome is surface-modified, thereby decomposition of encapsulated drugs or genes can be suppressed. Thus, the liposome for pulmonary administration of the invention also has advantage in view of high stability of the encapsulated drugs or genes.

BRIEF DESCRIPTION OF THE DRAWING

FIG. 1 is a graph showing the evaluation results of Test Example 1 measuring the behaviors of polymer-modified liposomes of Examples 1 and 2 and an unmodified liposome of Comparative Example 2 in rats' lungs.

BEST MODE FOR CARRYING OUT THE INVENTION

The invention will now be described in detail below.

In the liposome for pulmonary administration of the invention, the number of lipid bilayers is not specifically limited as long as the liposome is a closed vesicle having a lipid bilayer membrane structure. It may be any of small unilamellar vesicles (SUV), large unilamellar vesicles (LUV), and multilamellar vesicles (MLV).

In the liposome for pulmonary administration of the invention, a component constituting the lipid bilayer is not specifically limited as long as it is generally used as a constituent component of a liposomal membrane. In particular, examples of the constituent components of the liposomal membrane include lipids, membrane stabilizers, charged materials, antioxidants, and membrane proteins.

The lipid which is a constituent component of the liposomal membrane is an essential component in the liposomal membrane, and examples thereof include phospholipids, glycolipids, sterols, and saturated or unsaturated fatty acids.

Specific examples of the phospholipid include phosphatidylcholines such as dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, and palmitoylstearoylphosphatidylcholine; phosphatidylglycerols such as dilauroylphosphatidylglycerol, dimyristoylphosphatidylglycerol, dipalmitoylphosphatidylglycerol, distearoylphosphatidylglycerol, dioleoylphosphatidylglycerol, dilinoleoylphosphatidylglycerol, myristoylpalmitoylphosphatidylglycerol, myristoylstearoylphosphatidylglycerol, and palmitoylstearoylphosphatidylglycerol; phosphatidylethanolamines such as dilauroylphosphatidylethanolamine, dimyristoylphosphatidylethanolamine, dipalmitoylphosphatidylethanolamine, distearoylphosphatidylethanolamine, dioleoylphosphatidylethanolamine, dilinoleoylphosphatidylethanolamine, myristoylpalmitoylphosphatidylethanolamine, myristoylstearoylphosphatidylethanolamine, and palmitoylstearoylphosphatidylethanolamine; phosphatidylserine; phosphatidic acid; phosphatidylinositol; sphingomyelin; cardiolipin; egg yolk lecithin; soybean lecithin; and hydrogenated products thereof.

Specific examples of the glycolipid include glyceroglycolipids such as diglycosyldiglyceride, digalactosyldiglyceride, galactosyldiglyceride, and glycosyldiglyceride; glycosphingolipids such as galactosylcerebroside and ganglioside; stearylglucoside; and esterified stearylglycoside.

Specific examples of the sterol include cholesterol, cholesteryl hemisuccinate, lanosterol, dihydrolanosterol, desmosterol, dihydrocholesterol, phytosterol, stigmasterol, zymosterol, ergosterol, sitosterol, campesterol, and brassicasterol. Particularly, the sterol has the action of stabilizing the liposomal membrane and modulating fluidity of the liposomal membrane, and thus it is preferred to be contained as a constituent lipid of the liposomal membrane.

Specific examples of the saturated or unsaturated fatty acid include saturated or unsaturated fatty acids having 10 to 22 carbon atoms, such as decanoic acid, myristic acid, palmitic acid, stearic acid, arachidonic acid, oleic acid, and docosanoic acid.

These constituent lipids of the liposome membrane may be used alone, or two or more kinds of them may be used in combination. Of these constituent lipids of the liposomal membrane, a combination of phospholipid(s) and sterol is preferable and a combination of phosphatidylcholine and cholesterol is more preferable. When phospholipid(s) and sterol are used in combination, the ratio of both is not specifically limited and, for example, the amount of sterol is from 1 to 100 mol, preferably from 5 to 50 mol, and more preferably from 10 to 30 mol, per 100 mol of the phospholipid(s).

The content of the constituent lipid of the liposome membrane is not specifically limited and, for example, it is from 1 to 100%, preferably from 60 to 95%, and more preferably from 70 to 90%, based on the total amount of the constituent components of the liposome membrane in terms of molar ratio.

A charged material is mixed so as to modulate electric charge of the liposome membrane and is optionally used as a constituent component of the liposomal membrane. As used herein, charged material means a membrane constituting component having an electric charge other than the phospholipid, glycolipid and sterol. The electric charge of the liposomal membrane can be modulated by employing, as a lipid serving as a constituent component of the liposome membrane, ionic phospholipids such as cholesteryl hemisuccinate, phosphatidylserine, phosphatidylinositol, and phosphatidic acid, and also can be modulated by using the charged material in place of the ionic phospholipids, or using the charged material in combination with the ionic phospholipids. Specific examples of charged materials which impart a positive charge include aliphatic primary amines such as laurylamine, myristylamine, palmitylamine, stearylamine, and oleylamine. Examples of charged materials which impart a negative charge include dialkyl(C14-18) phosphate esters such as dicetyl phosphate. Of these charged materials, dialkyl phosphate esters, particularly dicetyl phosphate, are suited for use in the liposome for pulmonary administration of the invention since the use of such charged materials can form a negatively charged liposome, thereby efficiently modifying the surface of the liposome.

The proportion of the charged material contained in the liposomal membrane is not specifically limited and, for example, it is from 0 to 5%, preferably from 5 to 40%, and more preferably from 10 to 25%, based on the total amount of the constituent components of the liposomal membrane in terms of molar ratio.

An antioxidant can be contained so as to prevent oxidation of the liposomal membrane and are optionally used as a constituent component of the liposomal membrane. Examples of the antioxidant used as a constituent component of the liposomal membrane include butylated hydroxytoluene, propyl gallate, tocopherol, tocopherol acetate, tocopherol-enriched mixture, vitamin E, ascorbic acid, L-ascorbyl stearate, ascorbyl palmitate, sodium hydrogensulfite, sodium sulfite, sodium edetate, erythorbic acid, and citric acid.

The proportion of the antioxidant contained in the liposomal membrane is not specifically limited and, for example, it is from 0 to 40%, preferably from 5 to 20%, and more preferably from 2.5 to 10%, based on the total amount of the constituent components of the liposomal membrane in terms of molar ratio.

A membrane protein can be mixed for the purpose of addition of functions to the liposome membrane or stabilization of the liposomal membrane structure, and is optionally used as a constituent component of the liposommal membrane. Examples of the membrane protein include membrane surface protein, integral membrane protein, albumin, and recombinant albumin.

The proportion of the membrane protein contained in the liposomal membrane is not specifically limited and, for example, it is from 0 to 20%, preferably from 2.5 to 10%, and more preferably from 5 to 8%, based on the total amount of the constituent components of the liposomal membrane in terms of molar ratio.

In view of performing modification with chitosan efficiently and strongly, it is preferred to contain a component having a negative charge as a constituent component of the liposomal membrane. The liposome contains, as membrane constitute components, preferably phospholipids, sterol and a charged material capable of imparting a negative charge, and more preferably phosphatidylcholine, cholesterol and a dialkyl phosphate ester. According to the liposome containing such membrane constitute components, the surface modification of the liposome can be conducted efficiently and strongly, and also retention on the surface of lung tissue and transfer into lung tissue can be effectively controlled.

The particle diameter of the liposome used in the liposome for pulmonary administration of the invention (namely, the particle diameter of the liposome in a state where it is not surface-modified) may be appropriately set according to the kind of lipid to be used and the kind of polymer to be used for surface modification and, for example, it is from about 20 to 1,000 nm, preferably from about 50 to 500 nm, and more preferably from about 100 to 200 nm. The particle diameter of the liposome is measured by a dynamic light scattering method.

The liposome can be prepared, for example, by using known methods such as a thin-membrane hydration method, an ultrasonification method, an ethanol injection method, an ether injection method, a reverse-phase evaporation method, a surfactant method, a freezing/thawing method, and a thin-membrane hydration-ultrasonic method. The particle diameter of the liposome can be modulated by known methods such as an extrusion method, a French press method, and a homogenization method.

In the liposome for pulmonary administration of the invention, the surface of the liposome is modified with at least one polymer selected from the group consisting of terminal hydrophobized polyvinyl alcohols and chitosan (hereinafter, referred sometimes to as a surface-modification polymer). In the liposome for pulmonary administration of the invention, the surface of the liposome is modified by bonding the surface-modification polymer on the surface of the liposome through a hydrophobic bond, a hydrogen bond or an electrostatic bond.

Herein, the terminal hydrophobized polyvinyl alcohol means a polymer in which a hydrophobic group is bonded at the terminal of the polyvinyl alcohol. Specific examples of the terminal hydrophobized polyvinyl alcohol include polymers in which a hydrophobic group selected from an alkyl group, an alkoxy group, a carboxyalkyl group and a thioalkyl group is bonded at the terminal of the polyvinyl alcohol. Of these polymers, a polymer in which the hydrophobic group is a thioalkyl group is preferable. The alkyl group, alkoxy group, carboxyalkyl group and thioalkyl group which constitute the hydrophobic group having about 1 to 30 carbon atoms, preferably about 5 to 25 carbon atoms, and more preferably about 10 to 20 carbon atoms can be used. The alkyl group, alkoxy group, carboxyalkyl group and thioalkyl group which constitute the hydrophobic group may be linear or branched, and are preferably linear. The hydrophobic group of the terminal hydrophobized polyvinyl alcohol used in the invention is preferably an thioalkyl group having 1 to 30 carbon atoms, more preferably a linear thioalkyl group having 5 to 25 carbon atoms, and particularly preferably a linear thioalkyl group having 10 to 20 carbon atoms. The terminal hydrophobized polyvinyl alcohol for use in the present invention may be any polyvinyl alcohol having a hydrophobic group bonded to the terminal carbon atom of the polyvinyl alcohol. For example, when the hydrophobic group is a thioalkyl group, the sulfur atom of the thioalkyl group may be covalently bonded to the terminal carbon atom of the polyvinyl alcohol.

The degree of saponification of the polyvinyl alcohol moiety of the terminal hydrophobized polyvinyl alcohol is from 70 to 95 mol %, preferably from 80 to 95 mol %, and more preferably from 82 to 93 mol %. Furthermore, the degree of polymerization of the polyvinyl alcohol moiety of the terminal hydrophobized polyvinyl alcohol is from 100 to 1,000, preferably from 200 to 800, and more preferably from 300 to 600.

In the invention, these terminal hydrophobized polyvinyl alcohols may be used alone, or two or more kinds of them may be used in combination.

The terminal hydrophobized polyvinyl alcohol is a known compound, and is commercially available or prepared by a known production method.

Chitosan is a polysaccharide in which a glucosamine residue is bonded through a β1-4 bond. The degree of polymerization of the chitosan used for surface modification of the liposome is from 2 to 1,000, preferably from 50 to 900, and more preferably from 100 to 800 (about 20,000 to 150,000 in terms of molecular weight). Also, the degree of deacetylation of the chitosan is not specifically limited and, for example, it is 60% or more, preferably from 70 to 100%, and more preferably from 80 to 100%.

When more terminal hydrophobized polyvinyl alcohol exists on the liposomal surface, retention for a long time on the surface of lung tissue (e.g., on the bronchovesicular surface) becomes possible, meanwhile, when more chitosan exists on the liposomal surface, fast transfer into lung tissue becomes possible. Therefore, if more terminal hydrophobized polyvinyl alcohol exists on the liposomal surface, substances included into the liposome can act on the lung tissue surface or surface cells more efficiently. If more chitosan exists on the liposomal surface, transfer of substances included into the liposome into the lung tissue can be enhanced. Thus, the liposome surface-modified with the terminal hydrophobized polyvinyl alcohol is useful as a sustained release liposome for pulmonary administration or as a liposome for pulmonary administration targeting the lung tissue surface or surface cells. In addition, the liposome surface-modified with chitosan is useful as a fast-acting liposome for pulmonary administration or as a liposome for pulmonary administration targeting the surface or inside of lung tissue, particularly as a liposome for pulmonary administration targeting the inside of lung tissue.

The kind of surface-modification polymer in the liposome for pulmonary administration of the invention may be appropriately set based on intended intrapulmonary behavior taking the aforementioned transfer into lung tissue and retentivity on the surface of lung tissue into account. In the invention, the liposomal surface may be modified with either the terminal hydrophobized polyvinyl alcohol or chitosan alone, or a combination of both polymers.

The amount of surface-modification polymer in the liposome for pulmonary administration of the invention may be also appropriately set based on intended intrapulmonary behavior taking the aforementioned transfer into lung tissue and retentivity on the surface of lung tissue into account. For example, the surface-modification polymer may be used in the proportion of 1 to 300 parts by weight, preferably 5 to 250 parts by weight, and more preferably 10 to 200 parts by weight, per 100 parts by weight of the total amount of the constituent components of the liposomal membrane.

The surface midification of the liposome with the surface-modification polymer is carried out by sufficiently mixing the surface-modification polymer with the liposome in purified water or a buffer. Specifically, the liposome modified with the surface-modification polymer is formed by mixing an equal amount of an aqueous solution containing about 0.1 to 10% by weight of the surface-modification polymer and an aqueous solution containing about 1 to 10% by weight of the liposome, followed by stirring at 4 to 10° C. for 0.5 hours to 1 hour. Moreover, the liposome modified with the surface-modification polymer can be redispersed in purified water or a buffer after solid-liquid separation.

The liposome for pulmonary administration of the invention encapsulate drug(s) which are required to exert a pharmacological action in lung tissue or gene(s) for gene therapy in lung tissue, and is used as a carrier for pulmonary administration. In the present invention, gene(s) includes nucleic acids, such as siRNA, mRNA, rRNA, miRNA (micro RNA), ribozymes, antisense oligonucleotide, decoy oligonucleotide, plasmid DNA, peptide nucleic acid, triplex forming oligonucleotide (TFO), aptamer, and isolated DNA. The amount of drug(s) or gene(s) encapsulated in the liposome may be appropriately determined based on the kind of drug(s) or gene(s), and dosage.

In addition, methods of encapsulating drug(s) or gene(s) in the liposome modified with a surface-modification polymer are known and there can be used a method which is commonly used in this field. In particular, drug(s) or gene(s) is capsulated in the liposome by forming a liposome using a solution containing drug(s) or gene(s) and constituent components of the liposomal membrane. More specifically, a liposome preparation for pulmonary administration in which drug(s) or gene(s) are capsulated in the liposome for pulmonary administration of the invention can be prepared by following steps (i) and (ii):

(i) a step of mixing drug(s) or gene(s) with constituent components of the liposomal membrane to obtain drug(s) or gene(s) encapsulated liposome, and (ii) mixing the thus-obtained drug(s) or gene(s)-encapsulating liposome with the surface-modification polymer to modify the surface of the liposome with the surface-modification polymer.

Further, the liposome preparation for pulmonary administration, in which a drug(s) or gene(s) are encapsulated in the liposome for pulmonary administration of the invention, can also be prepared by mixing the drug(s) or gene(s), the constituent components of the liposomal membrane, and the surface-modifying polymer.

The liposome preparation for pulmonary administration in which drug(s) or gene(s) are encapsulated in the liposome for pulmonary administration of the invention is used by administering to the lung using an administration method such as transbronchial administration or nasal drip administration. Specifically, a therapeutically effective amount of the liposome preparation containing drug(s) or genes effective for treating a disease of lung tissue is administered to a lung of a patient suffering from the disease of lung tissue, thereby treating the disease of lung tissue.

EXAMPLES

The present invention will now be described in detail based on examples and the like, but the present invention is not limited thereto.

Example 1

Preparation of Liposome Modified with Terminal Hydrophobized Polyvinyl Alcohol

A liposome which has a lipid composition of distearoylphosphatidylcholine:cholesterol:dicetyl phosphate of 8:1:2 (molar ratio) and contains cholesteryl anthracene-9-carboxylate (CA) as a fluorescently-labeled substance was prepared by a membrane hydration-ultrasonic method. Specifically, distearoylphosphatidylcholine (103.2 mg), cholesterol (6.3 mg), dicetyl phosphate (17.9 mg), and CA (1 mg) were dissolved in chloroform, and then a thin lipid membrane was obtained under the conditions at 40° C. for 2 hours using an evaporator. Subsequently, the membrane was dried under reduced pressure overnight, and then the liposome was prepared by hydration with 6.4 mL of 100 mM acetate buffer.

The liposome thus obtained was surface-modified with a terminal hydrophobized polyvinyl alcohol (degree of saponification: 88%, degree of polymerization: 480, hydrophobic group: $C_{16}H_{33}S-$). Specifically, a 100 mM acetate buffer containing 20 g/L of terminal hydrophobized polyvinyl alcohol and a 100 mM acetate buffer containing 20.1 g/L of the liposome obtained above were mixed in equal proportions. Subsequently, the thus-obtained mixture was incubated for one hour at 10° C., obtaining the liposome modified with the terminal hydrophobized polyvinyl alcohol.

Example 2

Preparation of Liposome Modified with Chitosan

A chitosan-modified liposome was prepared in the same manner as in Example 1, except that chitosan (molecular weight: 150,000, degree of deacetylation: 85%) was used instead of the terminal hydrophobized polyvinyl alcohol. However, the particle diameter was increased by mixing an equal amount of a liposome suspension and buffer containing chitosan dissolved therein, and therefore an ultrasonic treatment was performed after mixing.

Test Example 1

Evaluation of Intrapulmonary Behavior in Rats

The polymer-modified liposome of Example 1 or 2 was transbronchially administered (15.63 µg CA/rat) to male Wistar rats (7 weeks old). Five hours after administration, the residual ratio of dosage (dose %) was calculated by measuring the CA concentration in lung tissue, bronchoalveolar lavage fluid (BALF), and bronchoalveolar lavage cells (BALC) using a spectrofluorometer (HITACHI F3010). For comparison, a test was performed in the same manner as described above, except that a liposome which is not modified with a polymer (membrane composition and CA content are same as those in Example 1) was used instead of the polymer-modified liposome (Comparative Example 1). The results are shown in FIG. 1.

As is apparent form the results shown in FIG. 1, in the polymer-modified liposome of Example 1, a stronger fluorescence derived from CA was detected in BALF as compared with Comparative Example 1. Thus, it was confirmed that the polymer-modified liposome of Example 1 is useful for exerting a pharmacological action on the surface or the surface cells of lung tissue, since they are able to retain on the surface of lung tissue for a long period of time.

In the polymer-modified liposome of Example 2, it was shown that more liposome transferred into the lung tissue because a stronger fluorescence derived from CA was observed in the polymer-modified liposome of Example 2 as compared with Comparative Example 1. Therefore, it was revealed that the polymer-modified liposome of Example 2 can be efficiently transferred into lung tissues at short time, and thus it is possible to efficiently deliver drugs, for example, which are not easily transferred into lung tissue, into lung tissue.

The invention claimed is:

1. A method for treating a disease of lung tissue, comprising the step of administering to a lung of a patient suffering from the disease of lung tissue and needing fast-transfer of a drug or a gene into the lung tissue a therapeutically effective amount of a liposome preparation for pulmonary administration in which a drug or a gene is encapsulated in a liposome having a liposome membrane surface modified with a chitosan, thereby transferring the drug or the gene to the inside of a lung tissue,
    wherein the liposome contains the chitosan in a proportion of 5 to 250 parts by weight, per 100 parts by weight of a total amount of all constituent components of the liposomal membrane; and
    wherein the chitosan has a molecular weight from 100,000 to 150,000 daltons and a degree of deacetylation of 80% to 100%.

2. The method for treating a disease of lung tissue according to claim 1, wherein the liposome contains a phospholipid as a constituent component of a liposomal membrane.

3. The method for treating a disease of lung tissue according to claim 1,
    wherein the liposome for pulmonary administration contains phosphatidylcholine, cholesterol and a dialkyl phosphate ester as constituent components of the liposomal membrane.

4. The method for treating a disease of lung tissue according to claim 1, wherein the gene is at least one nucleic acid selected from the group consisting of siRNA, mRNA, rRNA, micro RNA, ribozymes, antisense oligonucleotide, decoy oligonucleotide, plasmid DNA, peptide nucleic acid, tri plex forming oligonucleotide, aptamer, and isolated DNA.

5. The method for treating a disease of lung tissue according to claim 1, wherein the lung administrated the liposome is that of the patient needing fast-transfer of the gene into the lung tissue.

* * * * *